United States Patent [19]
Yasui

[11] Patent Number: 5,960,578
[45] Date of Patent: Oct. 5, 1999

[54] FISHING EQUIPMENT CONTAINING GERMICIDAL AGENT

[75] Inventor: Toshihiko Yasui, Tondabayashi, Japan

[73] Assignee: Shimano Inc., Sakai, Japan

[21] Appl. No.: 08/871,663

[22] Filed: Jun. 9, 1997

[30] Foreign Application Priority Data

Jun. 11, 1996 [JP] Japan ................................... 8-149360
Dec. 25, 1996 [JP] Japan ................................... 8-345810

[51] Int. Cl.⁶ .................................................. A01K 87/08
[52] U.S. Cl. ............................................................ 43/23
[58] Field of Search ..................................................... 43/23

[56] References Cited

U.S. PATENT DOCUMENTS

| | | | |
|---|---|---|---|
| 4,034,079 | 7/1977 | Schoonman | 424/83 |
| 4,467,548 | 8/1984 | Tabor | 43/23 |
| 5,296,238 | 3/1994 | Sugiura | 424/604 |
| 5,392,556 | 2/1995 | Ozeki et al. | 42/22 |
| 5,441,717 | 8/1995 | Ohsumi | 423/306 |
| 5,535,781 | 7/1996 | Paterson | 137/624.11 |

FOREIGN PATENT DOCUMENTS

| | | |
|---|---|---|
| 362064845 | 3/1987 | Japan . |
| 404149272 | 5/1992 | Japan . |
| 405001245 | 1/1993 | Japan . |
| 407041402 | 2/1995 | Japan . |

*Primary Examiner*—Jack W. Lavinder
*Attorney, Agent, or Firm*—Shinjyu An Intellectual Property Firm

[57] ABSTRACT

Handles and grips for fishing equipment having antibacterial and antifungal properties are disclosed. The grips are formed from a synthetic resin in which one or more germicidal agents have been added.

11 Claims, 9 Drawing Sheets

FISHING EQUIPMENT CONTAINING GERMICIDAL AGENT

BACKGROUND OF THE INVENTION

1. Field of the Invention

This invention relates to fishing equipment, and more particularly to a grip for fishing equipment which has germicidal properties.

2. Related Art

People who engage in fishing as a leisure activity often use a number of different types of fishing equipment during their outings. For example, they may carry a bait box for storing fishing bait, a cooler for storing the fish that they catch, a hand-held fishing net, and an equipment box in which they store line, weights, lures and the like. Of course, all of these items are usually carried by means of a handle their outer surface. Likewise, fishing rods used for boat fishing or salt water fishing typically include a grip formed above or below the reel seat.

Generally speaking, these types of grips are formed from natural cork or a synthetic resin such as urethane rubber, EVA, soft vinyl chloride, chlorosulfonated polyethylene or the like. These types of grips are molded as a separate unit and fitted around the main body of the equipment in question, or molded together with the main body of the equipment as an integrated unit.

This type of fishing equipment is often used on boats or on the shore, where the humidity is often high. In these environments, the fishing equipment is often handled by persons with hands soiled by bait, fish, or other organic matter, and thus the equipment often becomes malodorous due to the propagation of bacteria or fungus. In order to prevent this, it is conceivable to spray a germicide onto the grip before or after use. However, since the fishing equipment is generally washed with water after use, the germicide is also washed off, thus negating the effect of these sprays.

SUMMARY OF THE INVENTION

An object of the present invention is to provide a grip or handle for fishing equipment that has germicidal properties.

Another object of the present invention is to provide a grip or handle for fishing equipment that has germicidal properties that last for a prolonged period of time.

According to a first aspect of the present invention, a fishing rod includes at least one grip attached to the fishing rod, the grip formed from a synthetic resin and a germicidal agent.

According to a second aspect of the present invention, the synthetic resin is an elastomer.

According to a third aspect of the present invention, the elastomer is a thermoplastic styrene block copolymer.

According to a fourth aspect of the present invention, the germicidal agent is an inorganic porous complex which includes silver ions.

According to a fifth aspect of the present invention, the germicidal agent is one selected from the group consisting of a silver-alumino-silicate complex, a silver-zeolite complex, and a silver-zirconium phosphate complex.

According to a sixth aspect of the present invention, a fishing accessory includes a main body and a grip portion, wherein at least the grip portion is formed from a synthetic resin and a germicidal agent.

According to a seventh aspect of the present invention, the synthetic resin is formed by melting the synthetic resin together with pellets containing the germicidal agent.

According to a eighth aspect of the present invention, wherein at least the grip portion includes a coating on a surface thereof, the coating containing the germicidal agent.

According to a ninth aspect of the present invention, the main body includes a thermally insulated container, and the grip portion is a handle for carrying the thermally insulated container.

According to a tenth aspect of the present invention, the main body is a storage bag, and the grip portion is a handle for carrying the storage bag.

According to a eleventh aspect of the present invention, the main body is a fishing net, and the grip portion is a handle attached to the fishing net.

According to a twelfth aspect of the present invention, the main body is a fishing reel, and the grip portion is at least one handle grip attached to said fishing reel.

These and other objects and advantages of the present invention will become clear by the following description of preferred embodiments of the present invention with reference to the accompanying drawings.

DETAILED DESCRIPTION OF THE PREFERRED EMBODIMENTS

A first embodiment of the present invention will now be described with reference to the accompanying drawings.

Figure 1:
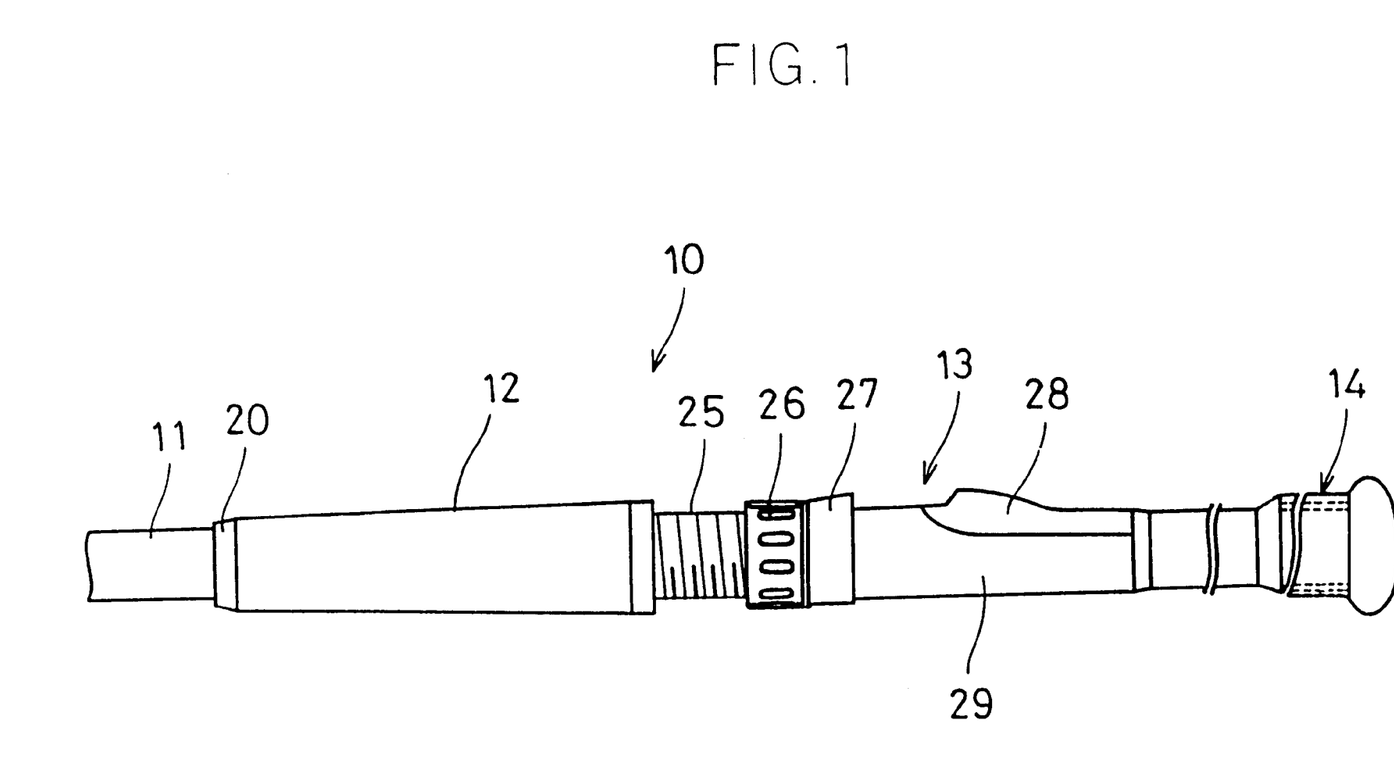
FIG. 1 is a fragmentary side view of a proximal end portion of a fishing rod according to one embodiment of the present invention.

As shown in FIG. 1, a proximal end 10 of a fishing rod includes a rod main body 11, a front grip 12, a reel seat 13 and a rear grip 14, all of which are arranged on the outer peripheral surface of the rod main body 11.

Figure 2:
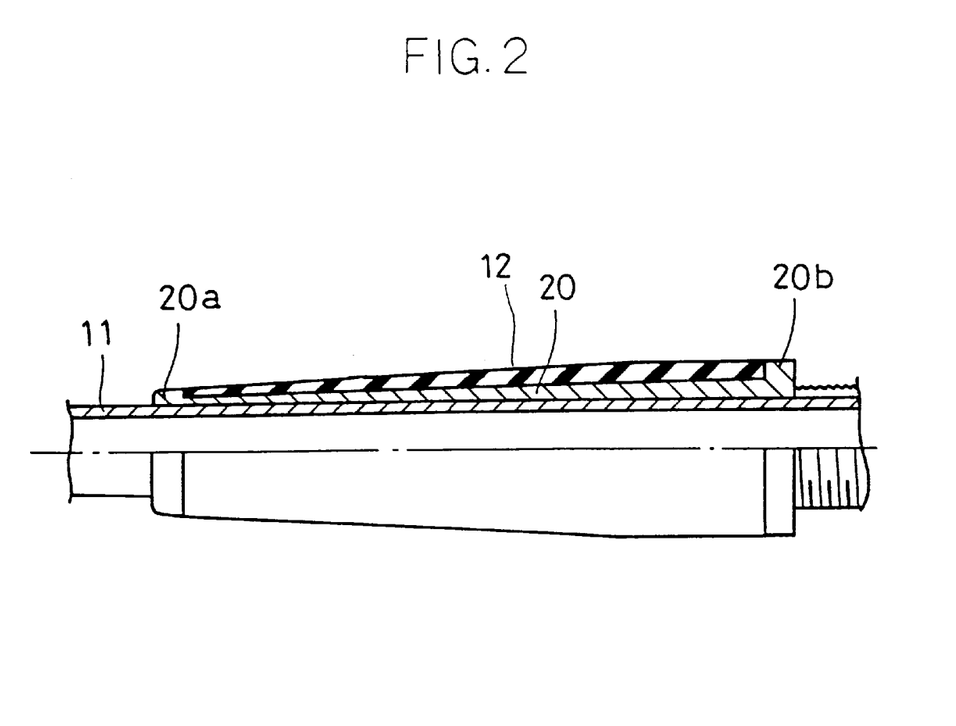
FIG. 2 is a sectional side view of a grip for the fishing rod depicted in FIG. 1.

The rod main body 11 is generally cylindrical in shape and has a tapered end. The front grip 12, as shown in FIG. 2, is a tapered cylindrical member having a smaller diameter at the front end of the fishing rod. The front grip 12 is molded together with a first cylinder 20 fitted around the peripheral surface of the rod main body 11. The front grip 12 is an elastomer formed from a synthetic resin containing an antibacterial and antifungal (hereinafter, germicidal) material.

The synthetic resins which may be used to form this elastomer include, but are not limited to, rubber-based elastomers such as urethane rubber, styrene block copolymer-based thermoplastic elastomers such as ACTIMER and LEOSTOMER, and other elastomers such as SANTOPLAIN and RABARON. ACTIMER is especially preferred because an appropriate level of elastic force can be obtained even when the thickness of the grip is reduced, and because the durability and feel of a grip formed therefrom is excellent even when wet.

Inorganic agents can be used as the germicidal material, such as metals having germicidal properties (for example, silver and zinc) combined with calcium phosphate. Of these inorganic germicidal agents, silver-based inorganic agents having silver ions in a porous carrier are preferred. Particularly preferred are silver combined with a silica-alumina carrier, a zeolite carrier, or a zirconium phosphate carrier. These inorganic germicidal agents cause less skin irritation and offer improved durability, when compared with organic germicidal agents. In addition, silver-based inorganic germicidal agents rarely cause metal allergies when compared with inorganic germicidal agents containing metals other than silver.

The first cylindrical body 20 is a tapered cylindrical member formed by molding a resin such as ABS or Nylon 66, and includes collar projecting portions 20a and 20b at both ends. The outer peripheral surfaces of these collar portions 20a and 20b are flush with the outer peripheral surface of the front grip 12. By combining the front grip 12 with the first cylindrical body 20 and making these members flush with each other, the thickness of the front grip 12 can be reduced even when the diameter of the front grip 12 is larger than that of the rod main body 11.

The front grip 12 may be formed by molding resin pellets containing a germicidal material. A front grip 12 formed in this manner allows very little of the germicidal material to be lost, even when the front grip 12 is washed with water, and allows the germicidal properties of the front grip 12 to be maintained for a prolonged period of time. Moreover, when Actimer® is used, the thickness of the front grip 12 and the amount of germicidal material added can be reduced, thereby making it possible to make the production costs of the front grip 12 lower than those when other elastomers are used.

The reel seat 13, as shown in FIG. 1, includes a screw portion 25 fitted onto the outer peripheral surface of the rod main body 11, a nut 26 connected to the screw portion 25, a front seat 27 whose position can be adjusted by the nut 26, a second cylindrical body 28 fitted onto the rod main body 11 at a rear end of the screw portion 25, and an intermediate grip 29 fitted onto the outer peripheral surface of the second cylindrical body 28 in such a manner that part of the second cylindrical body 28 is exposed.

Figure 3:
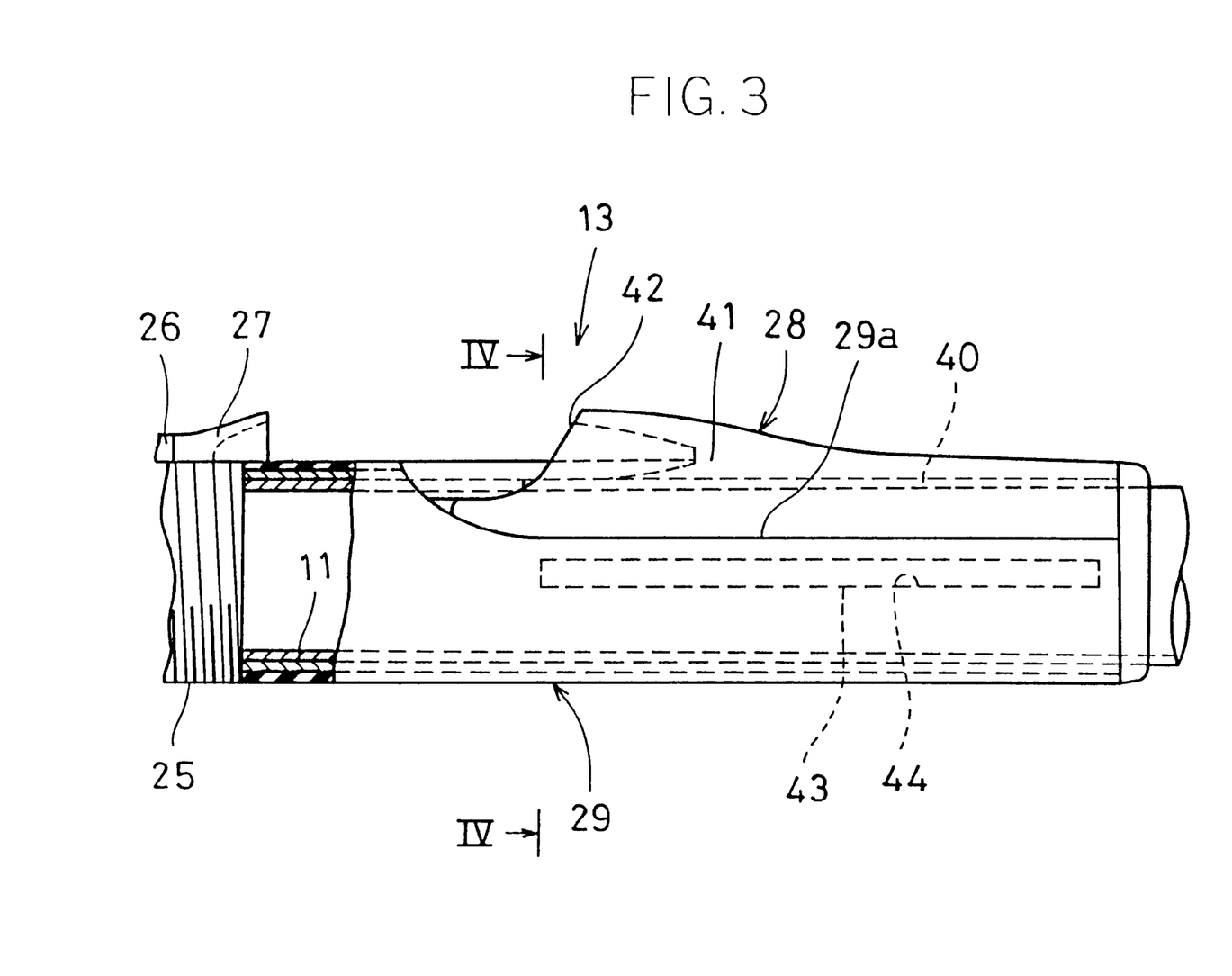
FIG. 3 is a partial side view of a reel seat for the fishing rod depicted in FIG. 1.

As shown in FIG. 3, the second cylindrical body 28 has a cylindrical main body portion 40 and a projection portion 41 projecting outward from the top of the main body portion 40. The projection portion 41 includes a rear seat 42 which opposes the front seat 27, and is formed such that it becomes flush with the peripheral surface of the intermediate grip 29. A reel is fixed to the rod main body 11 by fitting a reel attachment foot of the reel into the front seat 27 and the rear seat 42, and then rotating the nut 26 until the reel is securely seated. A positioning protrusion 43 is formed on both sides of the main body portion 40 of the second cylindrical body 28, and serves to position the intermediate grip 29.

Figure 4:
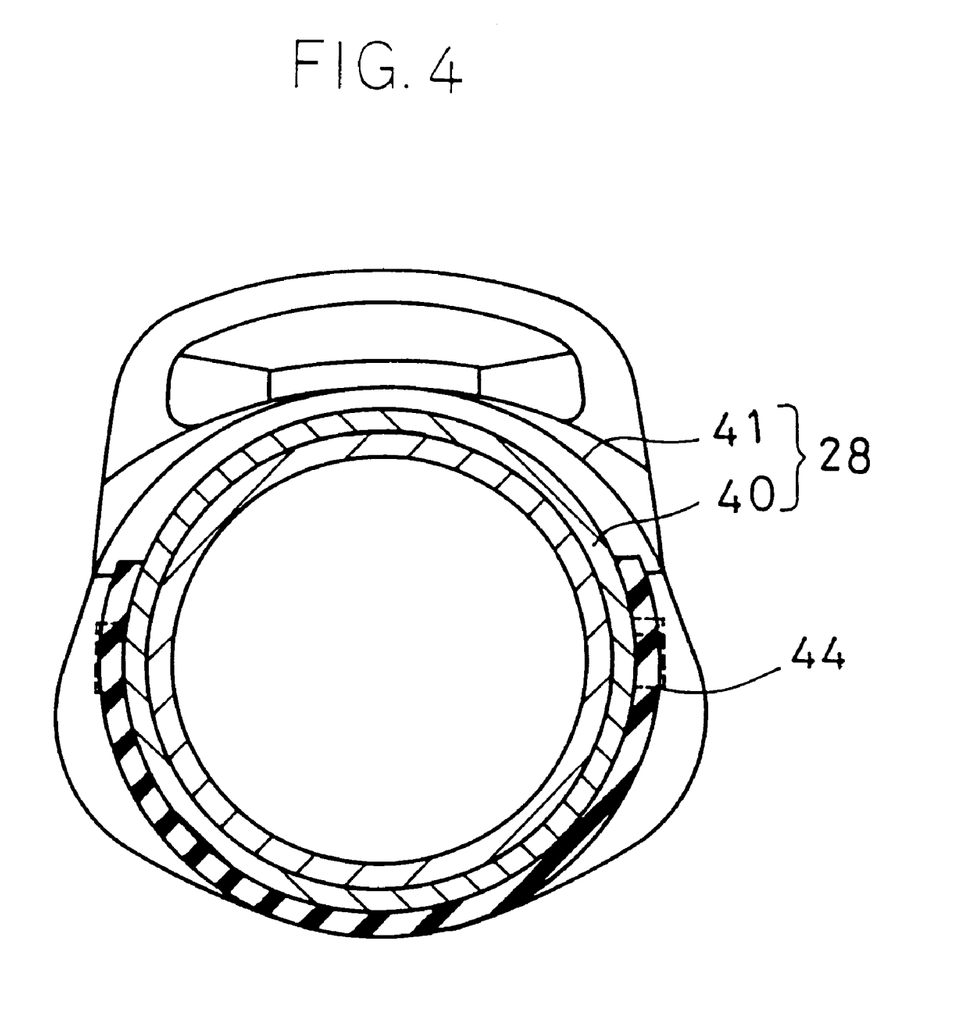
FIG. 4 is a sectional view of the fishing reel depicted in FIG. 1 taken along the line IV–IV in FIG. 3.

The intermediate grip 29 is made from an elastomer containing a germicidal material similar to that of the front grip 12. As shown in FIGS. 3 and 4, the intermediate grip 29 is a cylindrical member having slightly protruding side portions, and an opening 29a. The opening 29a is formed such that it becomes flush with the projection portion 41 where the projection portion 41 of the second cylindrical body 28 is exposed. A positioning groove 44 is formed in the interior peripheral surface of the intermediate grip 29, and is fitted onto the positioning protrusion 43.

The rear grip 14 is a cylindrical member having a cap which is fitted and bonded to the bottom of the rod main body 11 with an adhesive.

In this first embodiment, since three grips 12, 29 and 14 are made from an elastomer containing a germicidal material, they can maintain germicidal properties for a prolonged period of time.

A second embodiment of the present invention will now be described.

Figure 5:
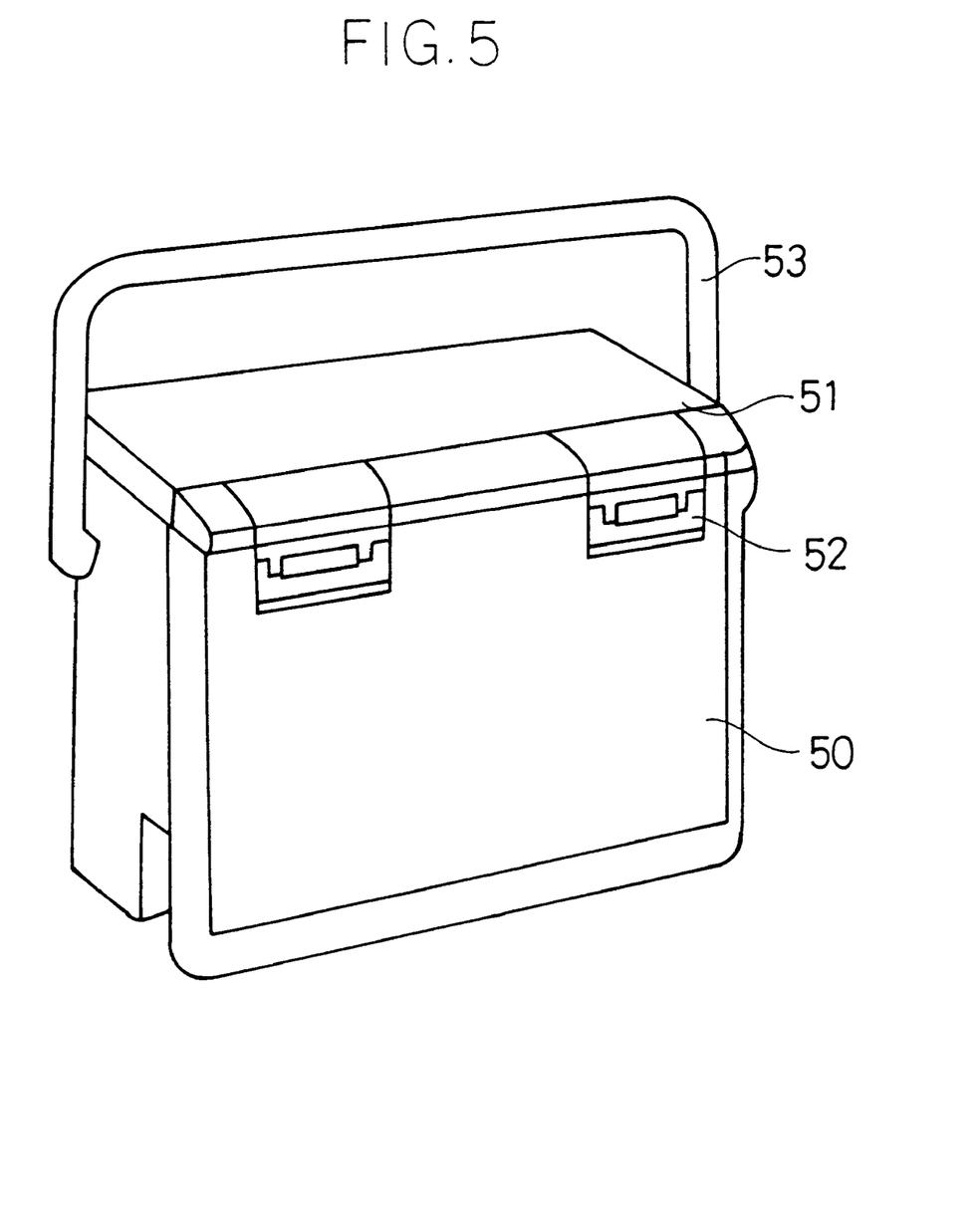
FIG. 5 is a perspective view of a cooler according to another embodiment of the present invention.

As shown in FIG. 5, a cooler includes a main body 50, a lid 51 which can be opened and closed by hinges (not shown), hook portions 52 for securely attaching the main body 50 to the lid 51, and a handle 53 connected to the main body 50.

The main body 50 and the lid 51 of the cooler are formed from a synthetic resin such as polypropylene, and includes an insulating material such as foamed polyurethane. The cooler can be used for storing fish or other temperature sensitive items.

The hook portions 52 can be provided at a plurality of sites on the main body 50 or the lid 51, and are formed from a synthetic resin such as polypropylene. The hook portions 52 can be formed individually and then fixed to the main body 50, or formed integrally therewith.

The handle 53 is connected to both end surfaces of the main body 50 with screws (not shown) or the like and is pivotable around those points. The handle 53 is a grip portion which is held by a user to carry the cooler, and is formed by molding a thermoplastic resin such as polypropylene with a germicidal material. The germicidal material is the same as that described in the first embodiment and its description is therefore omitted.

Like the fishing rod described above, because the handle 53 of the cooler is made from a synthetic resin containing a germicidal material, it can maintain germicidal properties for a prolonged period of time. And although a synthetic resin containing a germicidal agent is used only in the handle 53 in the second embodiment, it may be used in other portions of the cooler as well.

A third embodiment of the present invention will now be described.

Figure 6:
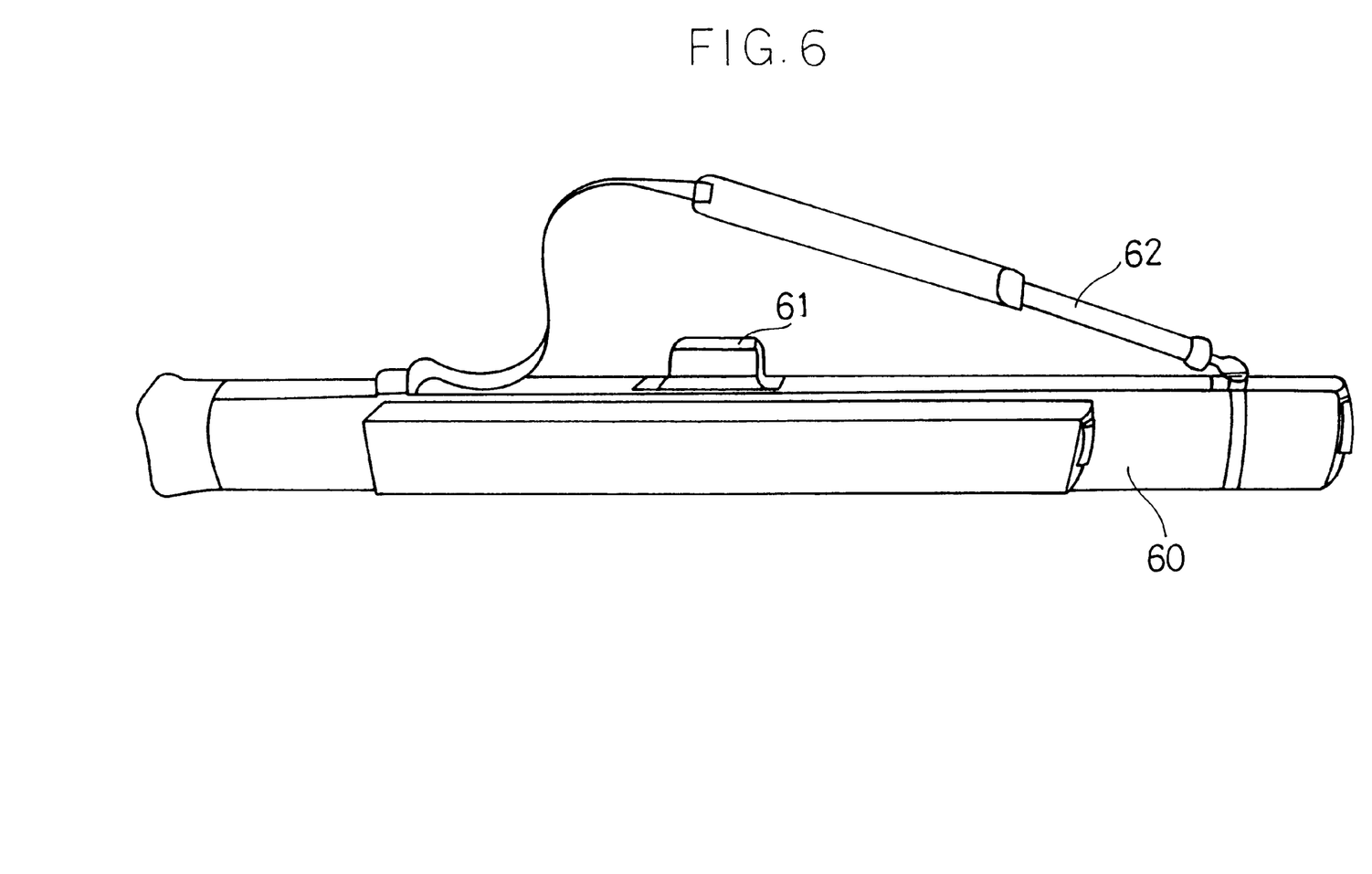
FIG. 6 is a side view of a bag for storing a fishing rod according to yet another embodiment of the present invention.

A fishing rod bag shown in FIG. 6 includes a main body 60 for storing one or more fishing rods, a grip 61 positioned on a top surface of the main body 60, and a strap portion 62 fixed at front and rear sides of the main body 60. The main body 60 is generally cylindrical in shape, and the strap portion 62 is formed like a belt so that a user can carry the bag on his or her shoulder. The main body 60 and the strap portion 62 are made from a synthetic fiber such as nylon treated with PVC.

The grip 61 allows a user to hold the bag 60 by hand, and is made by molding a thermoplastic resin such as polypropylene with a germicidal material. The germicidal material is the same as that of the first and second embodiments and its description is therefore omitted.

Like the previous embodiments, because the grip 61 of the fishing rod bag according to this embodiment is formed from an elastomer containing a germicidal material, very little of the germicidal material is removed by washing with water.

This allows it to maintain its germicidal properties for a prolonged period of time. In addition, although a synthetic resin containing a germicidal agent is used only in the grip 61, it may be used in other portions of the bag. For example, a synthetic fiber such as nylon containing a germicidal agent may be used in the main body 60 and the strap portion 62.

A fourth embodiment of the present invention will now be described.

Figure 7:
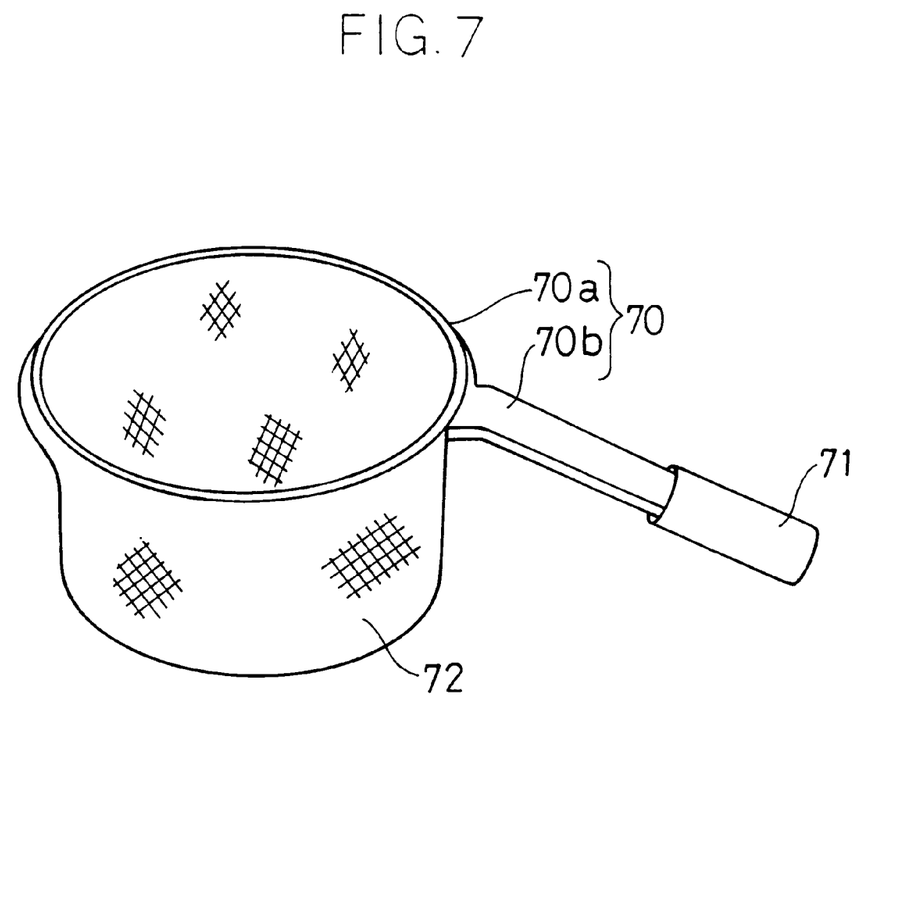
FIG. 7 is a perspective view of a fishing net according to yet another embodiment of the present invention.

As shown in FIG. 7, the main body of a fishing net includes a frame 70 having a net support portion 70a and a handle portion 70b extending outward from the net support portion 70a, a grip 71 disposed on the handle portion 70b, and a net 72 supported by the net support portion 70a of the frame 70. The grip 71 is made from an elastomer formed by injection molding a synthetic resin containing a germicidal material, and fixed to the end portion of the handle portion 70b of the frame 70. The germicidal material is the same as that of the first, second and third embodiments and its description is therefore omitted. Because the grip 71 of the main body of the fishing net of this embodiment is made from an elastomer containing a germicidal material, it can maintain germicidal properties for a prolonged period of time.

A fifth embodiment of the present invention will now be described.

Figure 8:
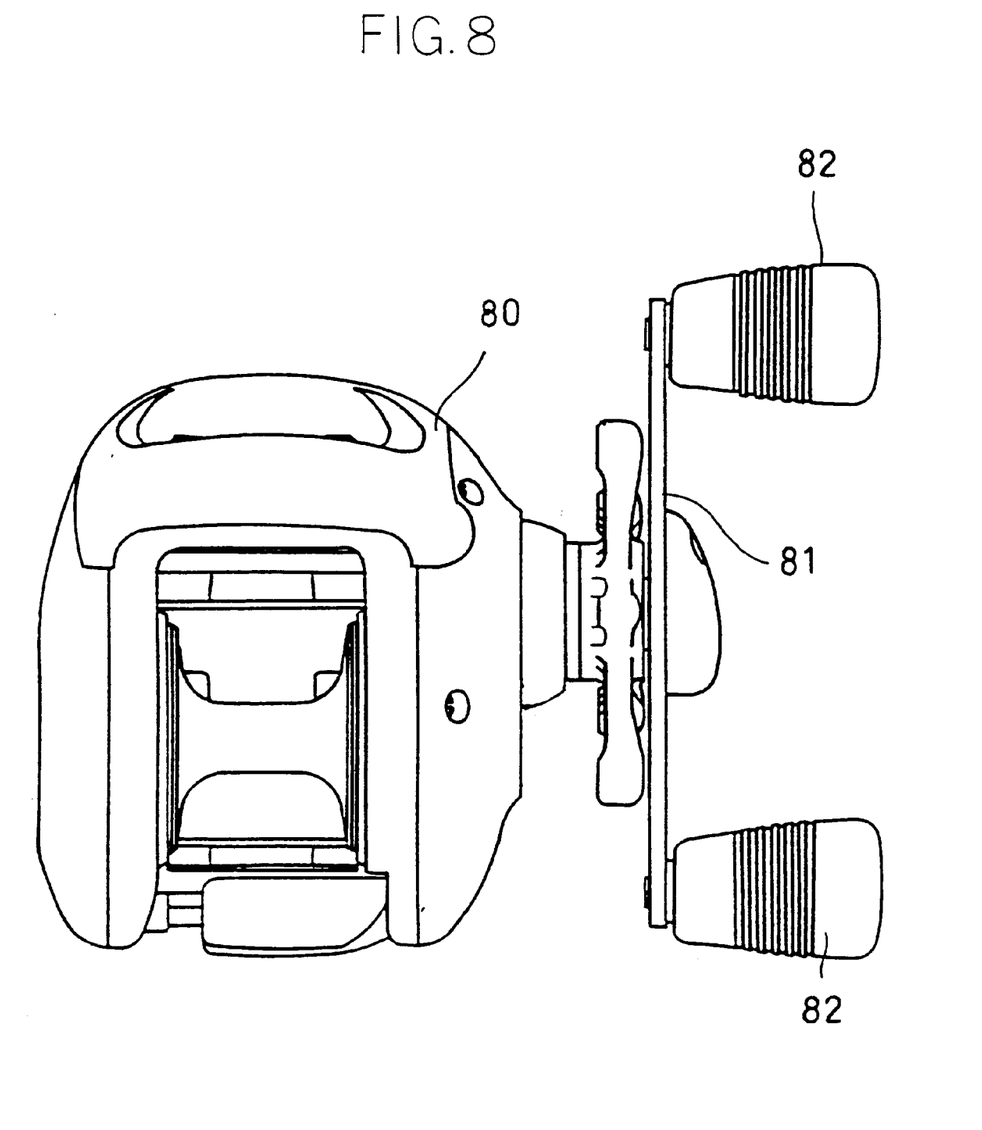
FIG. 8 is a side view of a fishing reel according to yet another embodiment of the present invention.

As shown in FIG. 8, a fishing reel has a reel main body 80, a rotary handle 81 disposed on a side of the reel main body 80, and a pair of handle grips 82 arranged at both ends of the rotary handle 81. The handle grips 82 are held by a user to rotate the rotary handle 81 around its axis. The handle grips 82 are made from an elastomer obtained by injection molding a synthetic resin containing a germicidal material. The germicidal material is the same as that of the first, second, third and fourth embodiments and its description is therefore omitted.

Like the fishing rod, cooler, bag and net, because the handle grips 82 of the fishing reel of this embodiment are made from an elastomer containing a germicidal material, it can maintain its germicidal properties for a prolonged period of time.

A sixth embodiment of the present invention will now be described.

Figure 9:
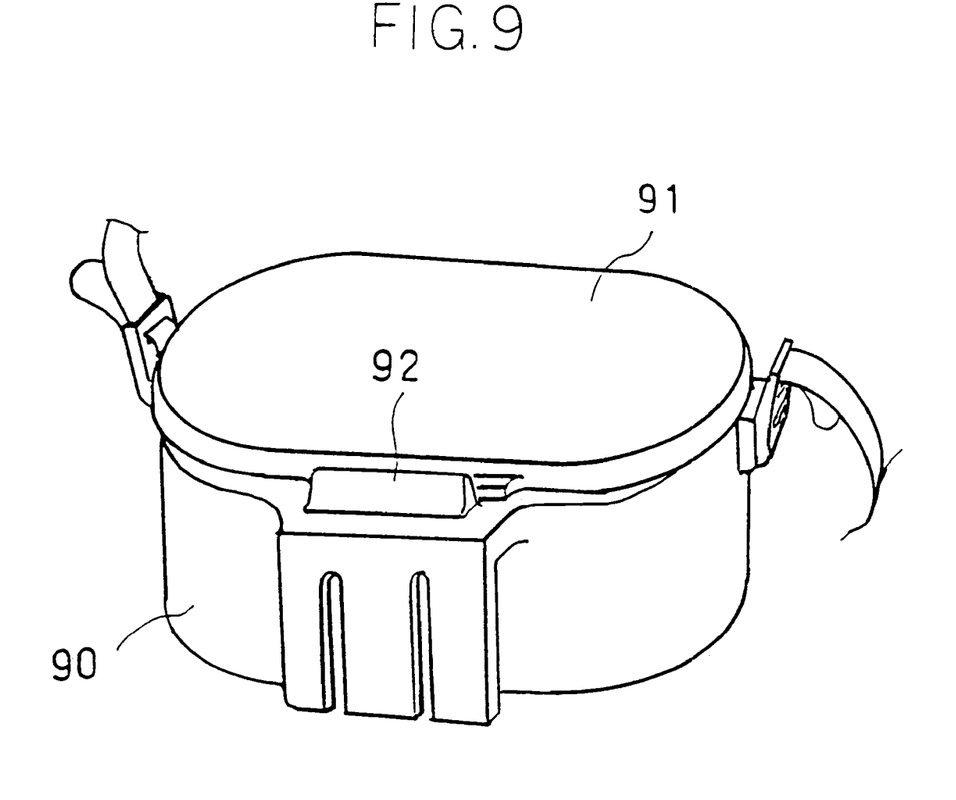
FIG. 9 is a perspective view of a fishing bait box according to a yet another embodiment of the present invention.

A fishing bait box shown in FIG. 9 has a main body 90, a lid 91 attached to the main body by hinges (not shown), and a hook portion 92 for securely attaching the main body 90 with the lid 91. The main body 90 and the lid 91 are formed from a synthetic resin such as polypropylene, and contains a heat insulating material such as foamed polyurethane. The fishing bait box may be used for storing fishing bait or other temperature sensitive items.

The hook portion 92 is arranged on an upper front portion of the main body 90 and made from a synthetic resin such as polypropylene. The hook portion 92 is formed separately, and then fixed onto the main body 90. The main body 90, the lid 91 and the hook portion 92 are made from a synthetic resin containing a germicidal material. The germicidal material is the same as that of the first, second, third, fourth and fifth embodiments and its description is therefore omitted.

Like with the other embodiments described above, because the main body 90, the lid 91 and the hook portion 92 are all made from a synthetic resin containing a germicidal material, it can maintain germicidal properties for a prolonged period of time. In particular, a fishing bait box which does not have a grip portion and thus must be carried by hand can have its germicidal properties improved by adding a germicidal material to the synthetic resin forming the entire fishing bait box.

The following examples and comparative example are provided to describe the germicidal effect of the present invention.

EXAMPLES 1 TO 4

A grip portion to be used on fishing equipment was obtained by preparing a thermoplastic resin ACTIMER, manufactured by Riken Vinyl Kogyo Co.) as a main starting material. Pellets containing about 10% by weight of an inorganic germicidal agent BACTEKIRANI, manufactured by Kanebo Co.) were then prepared, the active ingredient of the BACTEKIRANI being a complex of silver and zeolite. The ACTIMER and these pellets were mixed together in proportions of 0.3%, 0.5%, 1.0% and 3.0% by weight, respectively, and thermally molded to obtain the grip portion.

EXAMPLES 5 TO 8

Pellets containing about 10% by weight of an inorganic germicidal agent NOVALON, manufactured by Toa Gosei Co.) were prepared, the active ingredient of the NOVALON being a complex of silver and zirconium. As in examples 1 to 4, ACTIMER and these pellets were mixed together in proportions of 0.3%, 0.5%, 1.0% and 3.0% by weight, respectively, and thermally molded to obtain a grip portion.

EXAMPLE 9

Pellets containing about 10% by weight of organic germicidal agents (Hoxter HP and Irgazan, manufactured by Hokko Co.) were prepared. ACTIMER and 0.2% by weight of these pellets were mixed together and thermally molded to obtain a grip portion.

Comparative Example

A grip portion for fishing equipment was obtained by thermally molding a thermoplastic resin without any germicidal agent added.

Details of the above examples 1 to 9 and the comparative example are shown in Table 1.

TABLE 1

| Sample | Germicidal agent | Amount added (% by weight) |
|---|---|---|
| Example 1 | BACTEKIRANI | 0.3 |
| Example 2 | BACTEKIRANI | 0.5 |
| Example 3 | BACTEKIRANI | 1.0 |
| Example 4 | BACTEKIRANI | 3.0 |
| Example 5 | NOVALON | 0.3 |
| Example 6 | NOVALON | 0.5 |
| Example 7 | NOVALON | 1.0 |
| Example 8 | NOVALON | 3.0 |
| Example 9 | Organic agent | 0.2 |
| Comparative Example | None | None |

A portion of each of the grip portions obtained in examples 1 to 9 and the comparative example were cut out to prepare a test sample piece. A solution containing E. coli bacteria and MRSA bacteria was applied to the surface of each test sample piece, the surface of each sample was covered by a strip of transparent film, and maintained at a temperature of 25° C. for 24 hours. Thereafter, the number of bacteria present in the solution on each sample piece was counted. The survival rate and reduction rate of the E. coli bacteria in each sample after 24 hours are shown in Table 2.

TABLE 2

| Example | Beginning bacteria count | Bacteria count after 24 hours | Percentage reduction |
|---|---|---|---|
| Example 1 | $8.2 \times 10^5$ | $5.9 \times 10^2$ | >99.9 |
| Example 2 | $8.2 \times 10^5$ | $2.6 \times 10^2$ | >99.9 |
| Example 3 | $8.2 \times 10^5$ | <10 | >99.9 |
| Example 4 | $8.2 \times 10^5$ | <10 | >99.9 |
| Example 5 | $8.2 \times 10^5$ | <10 | >99.9 |
| Example 6 | $8.2 \times 10^5$ | <10 | >99.9 |
| Example 7 | $8.2 \times 10^5$ | <10 | >99.9 |
| Example 8 | $8.2 \times 10^5$ | <10 | >99.9 |
| Example 9 | $8.2 \times 10^5$ | <10 | >99.9 |
| Comparative Example | $8.2 \times 10^5$ | $7.4 \times 10^5$ | 9.7 |

The survival rate and reduction rate of MRSA bacteria after 24 hours are shown in Table 3.

TABLE 3

| Example | Beginning bacteria count | Bacteria count after 24 hours | Percentage reduction |
|---|---|---|---|
| Example 1 | $6.7 \times 10^5$ | $2.3 \times 10^4$ | 96.6 |
| Example 2 | $6.7 \times 10^5$ | $1.7 \times 10^4$ | 97.5 |
| Example 3 | $6.7 \times 10^5$ | $3.8 \times 10^2$ | >99.9 |
| Example 4 | $6.7 \times 10^5$ | <10 | >99.9 |
| Example 5 | $6.7 \times 10^5$ | <10 | >99.9 |
| Example 6 | $6.7 \times 10^5$ | 47 | >99.9 |
| Example 7 | $6.7 \times 10^5$ | <10 | >99.9 |
| Example 8 | $6.7 \times 10^5$ | <10 | >99.9 |
| Example 9 | $6.7 \times 10^5$ | <10 | >99.9 |
| Comparative Example | $6.7 \times 10^5$ | $1.2 \times 10^5$ | 82.1 |

As is evident from Table 2, the number of *E. coli* bacteria was reduced by 99.9% after 24 hours, in comparison with a reduction rate of 9.7% for the comparative example, which did not have a germicidal agent added.

As is evident from Table 3, the number of MRSA bacteria was reduced from 96.6% to 99.9% after 24 hours, in comparison with a reduction rate of 82.1% for the comparative example, which did not have an germicidal agent added. It can be seen that when 1.0% or more by weight of an germicidal agent containing silver and zeolite is included in the grip portion, its germicidal effect is especially good.

The gas resistance of the germicidal material of the present invention will now be described.

A test sample piece was prepared by cutting out a piece of each of the grip portions obtained in the above examples 1 to 9 and comparative example. Each test sample piece and a discoloration promoting agent were placed in a 100 cc. flask and sealed. The discoloration promoting agent consists of approximately 5 cc of distilled water placed onto a 10 g piece of cardboard containing one or more sulphur-based compounds. The water will dissolve the sulphur-based compound and produce sulphur-containing gases inside the flask. The discoloration of each sample piece by these sulphur-containing gases was evaluated visually. Each test sample piece was kept at room temperature (about 25° C.) and at a constant temperature of 50° C. Each test sample piece was kept for 336 hours (2 weeks).

The result of the discoloration of each sample when no discoloration promoting agent is added is shown in Table 4, and the result of discoloration of each sample when the discoloration promoting agent is added is shown in Table 5.

The discoloration of each sample piece was evaluated visually according to the following three criteria.

+: Discoloration is observed.
±: Slight discoloration is observed.
−: No discoloration is observed.

TABLE 4

| Example | Room Temperature | 50 C.° |
|---|---|---|
| Example 1 | − | − |
| Example 2 | − | − |
| Example 3 | − | − |
| Example 4 | − | − |
| Example 5 | − | − |
| Example 6 | − | − |
| Example 7 | − | − |
| Example 8 | − | − |
| Example 9 | − | − |
| Comparative Example | − | − |

TABLE 5

| Example | Room Temperature | 50 C.° |
|---|---|---|
| Example 1 | − | − |
| Example 2 | − | − |
| Example 3 | − | − |
| Example 4 | − | − |
| Example 5 | − | ± |
| Example 6 | − | − |
| Example 7 | − | − |
| Example 8 | − | ± |
| Example 9 | − | ± |
| Comparative Example | − | ± |

As is evident from Tables 4 and 5, when no discoloration promoting agent is added, no discoloration of is observed. When the discoloration promoting agent is added, discoloration was observed in the comparative example whereas no discoloration was observed at 50° C. in the test samples of Examples 1 to 4, which contain an inorganic germicidal agent having silver and zeolite. Slight discoloration was observed at 50° C. in the test samples of Examples 5 to 8, which contain a large proportion of an inorganic germicidal agent having silver and zirconium.

Although some differences were observed depending on type and content of the germicidal agent, the test samples of the present invention containing this type of agent can prevent discoloration. It cannot be asserted that the prevention of discoloration proves germicidal properties. However, when the fact that discoloration is observed in the test sample of comparative example is taken into consideration, the prevention of discoloration is related to germicidal properties.

A number of different modifications can be made to the present invention. Natural germicidal agents such as wasabi extract, *Phyllostachys pubescens* extract and chitosan, as well as organic halide compounds and paraoxy benzoic acid esters, may be used in place of silver-based inorganic germicidal agents.

In addition, the grip may be fixed to the equipment by means of an adhesive, as a separate molding, or integrated together with the main body thereof by making use of thermal shrinkage by thermal injection molding.

The main body portion or the grip portion of the equipment may have a germicidal coating placed on the surface thereof, formed by spraying an epoxy resin or the like containing a germicidal agent onto the outer surface thereof.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. A fishing rod, comprising:
   at least one grip attached to a fishing rod, said grip comprising a synthetic resin and a germicidal agent, wherein said grip portion is configured for engagement and manipulation by a human hand for carrying and manipulating the fishing rod, said synthetic resin is an elastomer that includes a thermoplastic styrene block copolymer and said germicidal agent is an inorganic porous complex which includes silver ions.

2. A fishing rod as in claim 1, wherein said synthetic resin is formed by melting said synthetic resin together with pellets containing said germicidal agent.

3. A fishing rod as in claim 1, wherein said germicidal agent is one selected from the group consisting of a silver-alumino-silicate complex, a silver-zeolite complex, and a silver-zirconium phosphate complex.

4. A fishing accessory comprising a main body and a grip portion, wherein at least said grip portion comprises a synthetic resin and a germicidal agent, wherein said grip portion is configured for engagement and manipulation by a human hand for carrying and manipulating the fishing accessory, and said germicidal agent is an inorganic porous complex which includes silver ions, and said synthetic resin is an elastomer that includes a thermoplastic styrene block copolymer.

5. A fishing accessory as in claim 4, wherein said synthetic resin is formed by melting said synthetic resin together with pellets containing said germicidal agent.

6. A fishing accessory as in claim 5, wherein at least said grip portion includes a coating on a surface thereof, said coating containing said germicidal agent and synthetic resin.

7. A fishing accessory as in claim 4, wherein said main body comprises a thermally insulated container, and said grip portion is a handle for carrying said thermally insulated container.

8. A fishing accessory as in claim 4, wherein said main body comprises a storage bag, and said grip portion comprises a handle for carrying said storage bag.

9. A fishing accessory as in claim 4, wherein said main body comprises a fishing net, and said grip portion comprises a handle attached to said fishing net.

10. A fishing accessory as in claim 4, wherein said main body comprises a fishing reel, and said grip portion comprises at least one handle grip attached to said fishing reel.

11. A fishing accessory as in claim 4, wherein said germicidal agent is one selected from the group consisting of silver-alumino-silicate complex, silver-zeolite complex and silver-zirconium phosphate complex.

* * * * *